(12) United States Patent
Hankla et al.

(10) Patent No.: US 11,413,424 B2
(45) Date of Patent: Aug. 16, 2022

(54) SYSTEM AND A METHOD FOR TURNKEY NEUROLOGICAL SOLUTION

(71) Applicant: Quantum Chromatics Corporation, Tyler, TX (US)

(72) Inventors: Matthew Ryan Hankla, Tyler, TX (US); Mary McInerny, Tyler, TX (US)

(73) Assignee: QUANTUM CHROMATICS CORPORATION, Tyler, TX (US)

( * ) Notice: Subject to any disclaimer, the term of this patent is extended or adjusted under 35 U.S.C. 154(b) by 357 days.

(21) Appl. No.: 16/416,411

(22) Filed: May 20, 2019

(65) Prior Publication Data

US 2020/0368487 A1 Nov. 26, 2020

(51) Int. Cl.
*A61M 21/00* (2006.01)
*A61N 5/06* (2006.01)
(Continued)

(52) U.S. Cl.
CPC .......... *A61M 21/00* (2013.01); *A61H 39/002* (2013.01); *A61N 5/0618* (2013.01); *H02S 10/40* (2014.12);
(Continued)

(58) Field of Classification Search
CPC .......... A61N 5/0618; A61N 2005/0645; A61N 2005/0647; A61N 2005/0648; A61N 2005/0652; A61N 2005/0666; A61M 21/00; A61M 21/02; A61M 2021/0027; A61M 2021/0044; A61M 2021/0055; A61M 2021/0072
See application file for complete search history.

(56) References Cited

U.S. PATENT DOCUMENTS 5,518,497 A * 5/1996 Widjaja ................ A61M 21/00 600/26
6,443,977 B1 * 9/2002 Jaillet .................. A61M 21/00 600/27
(Continued)

OTHER PUBLICATIONS

Notification of Transmittal of the International Search Report and the Written Opinion of the International Searching Authority dated Aug. 26, 2020, in connection with corresponding international Application No. PCT/US20/33748 (11 pp.).

*Primary Examiner* — Carrie R Dorna
(74) *Attorney, Agent, or Firm* — Maier & Maier, PLLC

(57) ABSTRACT

A system and a method of turnkey neurological solution to provide a variety of stimulations including photo-stimulation, binaural stimulation, and electro-acupuncture in wearable form, such as in glasses. Light may be generated from at least one light source powered by integrated photovoltaic cells and amplified light may be sent to a predetermined direction through the at least one angularly oriented optical window in which one face is covered by an optical film or coating. Also, the system and method may provide that, as an optical window is fabricated, photovoltaics may be fused directly to faces of the optical window for absorption of ambient light energy, and a light source may be fused into grooves on the edge of the optical window, with nanoelectrodes attached for electrical connections to controllers inserted in a housing. It may also be contemplated to provide binaural stimulation and electro-acupuncture effectors on the wearable device.

19 Claims, 4 Drawing Sheets

(51) Int. Cl.
*A61H 39/00* (2006.01)
*H02S 10/40* (2014.01)

(52) U.S. Cl.
CPC .............. *A61M 2021/0027* (2013.01); *A61M 2205/051* (2013.01); *A61M 2205/502* (2013.01); *A61M 2205/52* (2013.01); *A61N 2005/0626* (2013.01); *A61N 2005/0648* (2013.01); *A61N 2005/0652* (2013.01); *A61N 2005/0666* (2013.01)

(56) References Cited

U.S. PATENT DOCUMENTS

| | | |
|---|---|---|
| 6,471,716 B1 | 10/2002 | Pecukonis |
| 7,175,273 B2 | 2/2007 | Lee |
| 8,932,218 B1 | 1/2015 | Thompson |
| 9,528,876 B2 | 12/2016 | Micheels |
| 9,977,265 B2 | 5/2018 | Shiratori |
| 2005/0122469 A1 | 6/2005 | Brabec |
| 2012/0203310 A1 | 8/2012 | Pugh et al. |
| 2014/0277291 A1* | 9/2014 | Pugh ................ G02C 7/04 607/88 |
| 2017/0102562 A1 | 4/2017 | Ban et al. |

* cited by examiner

SYSTEM AND A METHOD FOR TURNKEY NEUROLOGICAL SOLUTION

BACKGROUND

Optogenetics is a biological technique that combines genetics and optics, and involves the use of light to control cells in living tissue, typically neurons. The field has been a subject of experiment since at least 1971, where experiments demonstrated laser activation of neurons within the intact tissue of Aplysia sea slugs. The field has been growing rapidly since the early 2000s, with optogenetics having been chosen as the "Method of the Year" by the interdisciplinary research journal Nature Methods and having been highlighted as a "Breakthrough of the Decade" in the highly regarded research journal Science. While many of the breakthroughs in this field have focused on stimulating genetically modified neurons with light-sensitive ion channels (allowing the activity of individual neuronal populations to be turned on or off), it is also being explored as a therapeutic tool for other conditions, most commonly for use in treating blindness and related conditions such as retinitis pigmentosa ("RP") and advanced dry age-related macular degeneration ("advanced dry-AMD"). For example, the RETROSENSE RST-001 therapy makes use of a genetically modified virus used to inject a gene for a light-sensitive algal protein, Channelrhodopsin-2 (ChR2), into the retinal cells of patients with RP or advanced-dry AMD, in such a manner that the retinal cells can be provided with the gene in question and can be given some amount of light sensitivity.

As the science of optogenetics is uncovering opportunities to make medications obsolete, there is one component that is hindering the realization of the science: typical solutions are not conducive to everyday activities. As noted, optogenetic neural therapies focus around the use of genetically encoded switches that allow neurons to be turned on or off with bursts of light, but these neurons have to actually be turned on or off at optimal times; there is little purpose in encoding a switch unless it will be flipped. It may be understood that eyes respond dependently upon individual wavelengths of light. Each wavelength of light stimulates a different electrochemical signal that is sent to the brain via the optic nerve, programmed by way of the eye's photoreceptors. Electrical activity of brain waves can be detected (for example, by integration of electrophysiology and functional MRI), and this data can be correlated to neurological symptoms. By sourcing a specific mid-range wavelength of light, brain activity can be tuned in a way to eliminate certain neurological symptoms, such as anxiety, ADHD (Attention Deficit Hyperactivity Disorder), depression, schizophrenia, or the like. However, detecting these conditions and applying the light rapidly enough to have any useful effect has thus far been difficult outside of laboratory conditions.

The same has likewise been true for many other forms of therapy that have been gaining ground in recent years. For example, binaural beats therapy is an emerging form of soundwave therapy in which two slightly different frequency tones are played in the left and the right ears. For example, it may be contemplated to play a 200 Hz tone in the left ear and a 210 Hz tone in the right. The binaural beat heard will then be the difference between the two frequencies, 10 Hz. Various benefits of binaural beats therapy have been noted in some patients, such as reduced stress or anxiety, with many proponents likening the effect to that of meditation. However, as the therapy has been currently implemented, a user will need to make use of a set of stereo headphones linked to a audio player device, which means that it is not a good idea for the user to employ the therapy in a situation where they are engaging in a task that requires the user to be alert or requires the full attention of the user, since the headphones will make the user unable to hear other noises that may require their full attention (such as, for example, the sirens of emergency vehicles or the horns of other drivers). This limitation, as well as the need for the user to practice it for a significant amount of time every day while being free of other distractions, have limited its application. It is often recommended that users perform the therapy around ~30 minutes per day for upwards of a month in order to see significant benefits, and continue to use it regularly as part of a maintenance practice. However, users suffering from many of the problems it can help correct, like stress or anxiety, often cannot guarantee that they will have this amount of time available or will be able to keep it free of distraction, and as such often these users do not stick with the therapy.

A third increasingly popular therapy is microcurrent electrical neuromuscular stimulation (MENS), often applied as micro-point stimulation (MPS) or electroacupuncture. MENS devices are used to send weak electrical signals into the body, applying very weak electrical currents to nerves using electrodes placed on the skin (in the case of many typical MENS devices) or placed subdermally (in the case of electroacupuncture). In electroacupuncture specifically, it may be contemplated that needles may be inserted into acupuncture points as per traditional acupunctural practice, but then the needles may be attached to a device that generates continuous electrical pulses via the needles, typically via detachable clips. These devices may provide different pulses at different intensities, depending on the condition being treated. Most commonly, pairs of needles may be stimulated simultaneously, usually for no more than 30 minutes at any one time. Certain studies have noted that, at most acupuncture points on most subjects, there were greater electrical conductance maxims than at control sites, indicating a potential correlation between acupunctural practice and MENS microcurrent that has led the two to be combined. However, MENS in general, and electroacupuncture in particular, are difficult to apply over an extended period of time and outside the supervision of a skilled technician, with the FDA Center for Devices and Radiological Health cautioning that the use of a high DC current in the system could lead to tissue damage and electrolysis if the system is not properly calibrated or is operated by an untrained practitioner.

SUMMARY

A system and a method for turnkey neurological solution to provide a variety of stimulations including photo-stimulation, binaural stimulation, and MENS (which in an exemplary embodiment may be electro-acupuncture) in a wearable form, such as in a set of glasses, may be shown and described. According to an exemplary embodiment, such a system and method may operate to generate light from at least one light source powered by integrated photovoltaic cells, send amplified light to a predetermined direction through the at least one angularly oriented optical window which has one face covered by optical film or coating, and integrate binaural stimulation and electro-acupuncture into the temples of the set of glasses, the "temples" being the long arms on the sides of the frame that extend from the hinge and over the ears. The system and method may also provide electricity from photovoltaic cells integrated into the temples while ensuring that the wearable device never needs to be recharged by connecting to the local utility grid network. In the system and method, as an optical window may be fabricated, photovoltaics may be fused directly to the faces of the optical window for absorption of ambient light energy, and a light source such as an LED array may be fused into grooves of the edge of the optical window with nanoelectrodes attached for electrical connections to controllers inserted in a housing.

Such a system may include: one or more optical windows; one or more light sources; and a housing. According to an exemplary embodiment, the housing has one or more controllers, one or more connectors, and one or more stems. In an exemplary embodiment, the one or more optical windows pass light generated by the one or more light sources, one or more optical windows are mounted on the housing, and one or more temples are extended from the housing, with the housing including at least one controller.

In another exemplary embodiment, a method for turnkey neurological solution may be described. Such a method may include: generating lights by one or more light sources; passing, by one or more optical windows, the generated light to a predetermined direction; and controlling, by one or more controllers, the one or more light sources.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Figure 1:
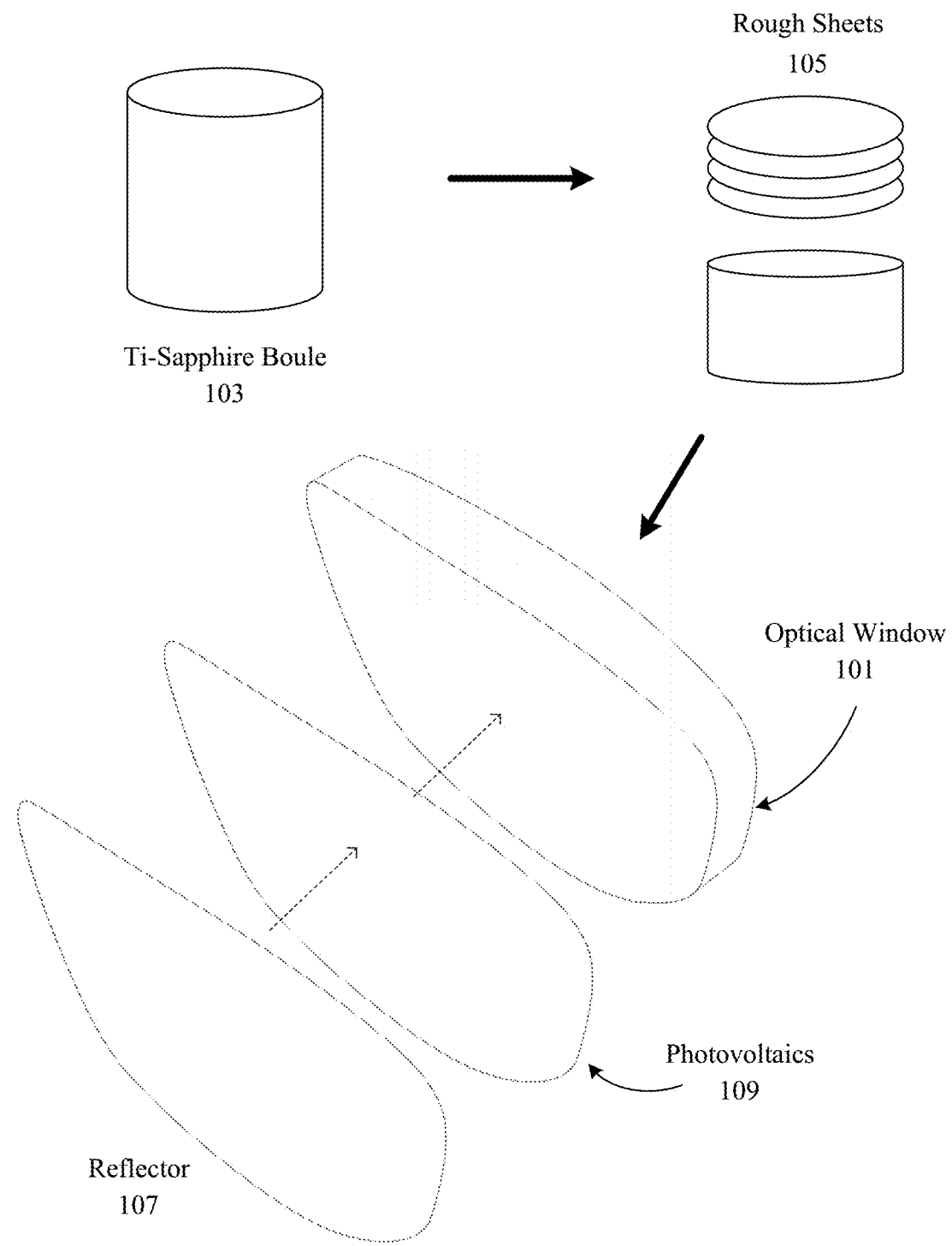
FIG. 1 is an exemplary schematic diagram showing a process of fabricating an optical window.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, the sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to at least one exemplary embodiment, a system and a method for turnkey neurological solution to perform various type of stimulations including photo-stimulation, binaural stimulation, and electro-acupuncture (or any other MENS device) in a wearable form, may be shown and described. Additionally, although exemplary embodiments may refer generally to titanium-doped sapphire (Ti-Sapphire) for a fabrication of an optical window, it will be appreciated that the exemplary embodiments of the optical window may be fabricated from any other desired crystal structures, such as, but not limited to, sapphires, rubies, or Neodymium-doped Yttrium Aluminum Garnet (NdYAG). Particularly, the optical window that may be formed from Ti-Sapphire material may be stimulated by a light source such as, but not limited to, LED arrays when the light source provides photons into the optical window. Photons pumped into the optical window may be amplified to stimulate an emission of new photons that are coherent to the photons pumped by the light source.

It may be contemplated that photovoltaic cells will convert ambient light energy in the environment into a direct current that can be used to power components without connecting to the local utility grid network. The photovoltaics may be formed using Gallium Arsenide (GaAs), and may have a quantum absorption efficiency that varies with respect to particular bandgaps. In an exemplary embodiment of a photovoltaic cell used in the present design, the quantum absorption efficiency may be roughly 94-97% efficient at the specific bandgap that an optical window of Ti-Sapphire shows in luminescing. This may, for example, allow a certain portion of the light provided via the LEDs and amplified via the Ti-Sapphire to be recycled by the photovoltaics with a high efficiency. Because a favorable temperature gradient may cause LEDs to electroluminesce with a high gain factor (often significantly greater than 100% electrical efficiency, sometimes up to around 325%) and since the photovoltaics may themselves have a high efficiency, this means that if all light could be captured, it may be possible to charge the device based on the thermal gradient alone. Thus, with 40% efficient light sources which are amplified with 300% gains via the optical window of Ti-Sapphire and which are absorbed at 94% efficiency from GaAs photovoltaics, the resulting gains may be over 100%. Such gain values may depend on the specifications of the gain medium which may be used (which may be based on, for example, the exact wavelengths of the light used for optogenetic purposes), but in many cases, particularly cases where specified wavelengths of light are to be used, the solid-state amplification may be increased substantially, increasing power outputs. It may thus be contemplated that a charging system may be implemented such that, when the glasses are folded, the LEDs and amplification media are placed in close proximity to the photovoltaics of the temples, allowing charging activity to take place if the LEDs can operate at a sufficiently high gain in the contemplated thermal environment.

The glasses (or other wearable device) may have hinges, which may be terminals that connect power from the photovoltaic cells to light sources snapped into the optical windows without hindering hinging functions. (For example, the hinges may be constructed from an electrically conductive material such as aluminum or copper.) Finally, a housing may be snapped around the edges of the optical window, with the housing enclosing the LEDs or other light emitters in order to generate various wavelengths of light.

Now referring to the Figures generally, a platform for turnkey neurological solution to perform various type of stimulations including photo-stimulation, binaural stimulation, and electro-acupuncture in a wearable form, may be shown and described. The platform may utilize a software application installed on a device. The device may include, but is not limited to, a mobile device, personal computer, or tablet. In some embodiments, the platform may be or may include a downloadable application and may operate across various operating systems and computing environments. For example, these environments may include iOS, Android, and personal/enterprise computing systems, including PC or Mac desktops and laptops. In other embodiments, the platform may operate in a purely or partially web-based environment (such as, for example, on a Linux server). The application may store user data on the device's local memory and/or in a cloud or enterprise-based storage system.

Turning now to exemplary FIG. 1, an exemplary schematic diagram showing a process of fabricating an optical window 101 may be shown and described. According to an exemplary embodiment, the process may include growth of a boule of optical amplification medium, such as a Ti-Sapphire boule, 103 to be cut into rough sheets 105. A rough sheet may be processed to form the optical window 101 which is configured to have a correct orientation to be most conducive to the luminescent incident angle that faces of the optical window 101 may give off. Exemplary embodiments may provide the optical window 101 in a thickness necessary to support the power outputs necessary for the application, for example, a rectangular window of 6-inch wide, 3-inch high, and 4.5 mm thick. In various exemplary embodiments, the amplification properties of the Ti Sapphire will be dependent upon the amount of material by volume used for each lens, the amount by which it is necessary to increase optical power, and the intended frequency of operation of the device components and the ability to charge the device components, either through use of an external power system or via a thermal gradient, in order to provide any necessary electro acupuncture shocks and binaural stimulations.

In still further exemplary embodiments, a front face of the optical window 101 may be covered by a reflector 107 in order to redirect illuminated light back to a predetermined direction. The reflector 107 may include coating with a light specific optical coating material or an optical film.

In additional exemplary embodiments, at least one photovoltaic cell 109 such as Gallium Arsenide (GaAs) photovoltaic cells may be grown or fused directly to the faces of the optical window 101 to absorb amplified energy. In an alternative exemplary embodiment, the at least one photovoltaic cell 109 may instead be a separate component, and may be interchangeable with other components. It may function to hold the photovoltaic layer 109, or any other applicable layers, within microns of the adjoining layer in order to achieve optimal absorption and functional efficiencies. For example, it may be contemplated that optomechanical housings may be used in order to retain each of an optically reflective coating, a photovoltaic cell, LEDs, and a sapphire lens, or a plurality of any or all of the above, within microns of the other layers. It may be contemplated that interchangeable optomechanical housings may be provided for each of the layers in order to save on cost, which may also provide a reduced cost as compared to using a fusion process to deposit the materials atomically onto one another.

Figure 2:
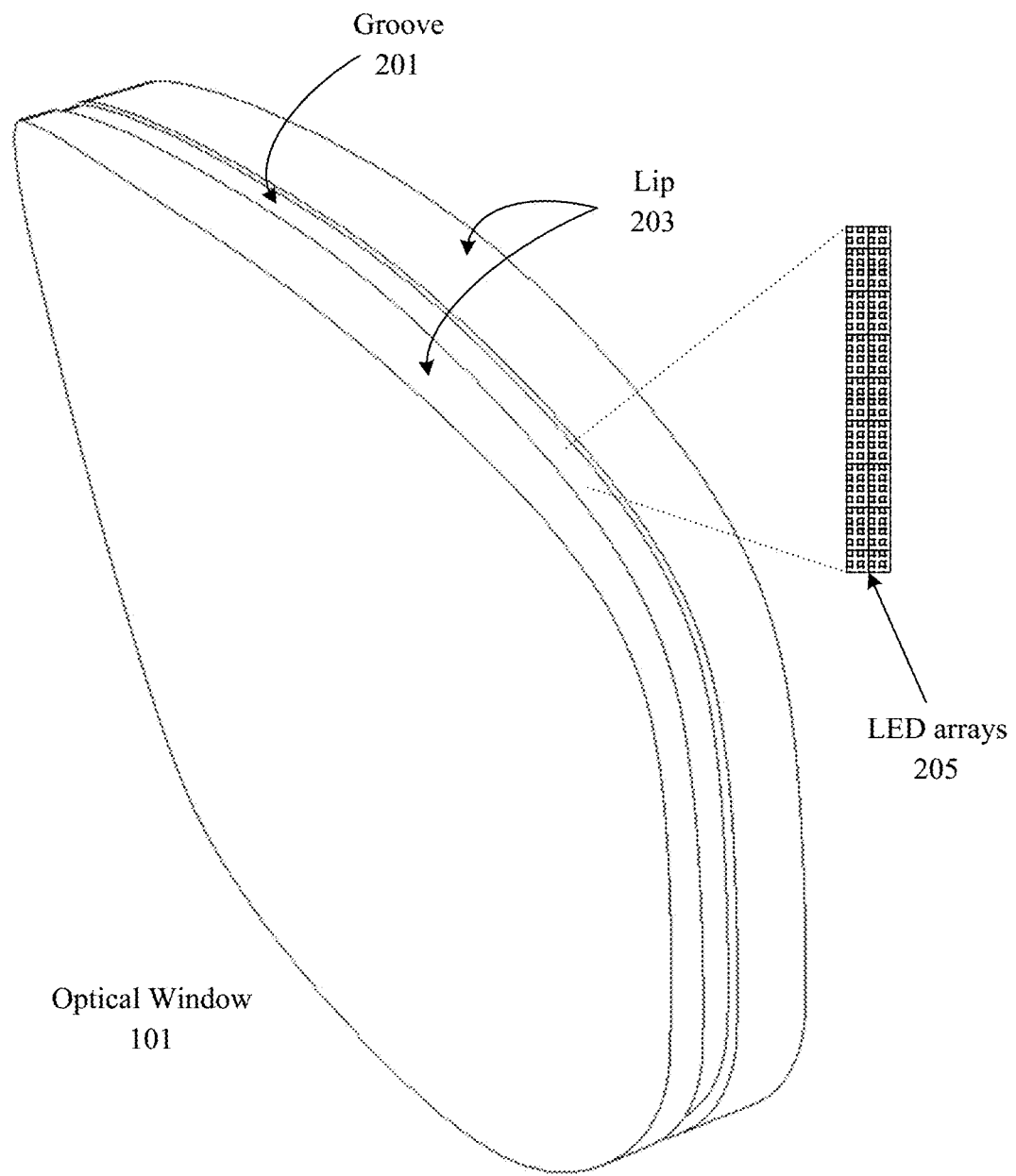
FIG. 2 is an exemplary schematic diagram showing an optical window with at least one groove and at least one lip, and LED arrays to be snapped into the optical window.

Turning now to exemplary FIG. 2, an exemplary schematic diagram showing an optical window 101 with at least one groove 201 and at least one lip 203, and LED arrays 205 to be snapped into the optical window 101 may be shown and described. According to an exemplary embodiment, faces of the optical window 101 may be polished and the at least one groove 201 is cut around outer edges of the optical window 101. The at least one groove 201 may include at least one lip 203 that allows the interchangeable LED arrays to be snapped into the at least one groove 201 around the outer edges of the optical window 101.

In still further exemplary embodiments, at least one groove 201 may be cut with such an angle to optimize efficiency of the incident angles of the LED arrays 205 which is snapped into the edges of the optical window 101. The at least one groove 201 and the at least one lip 203 may function as a "packaging" for the LED arrays 205, allowing for more seamless integration and interchange of the LED arrays 205. Additionally, the optical window 101 is also designed with a certain orientation that allows the equilibrant distribution of incoming light across the faces of the optical window 101, increasing the efficiency of harvesting the amplified light energy, for example, amplification accomplishing 101%-325% efficiencies.

In additional exemplary embodiments, the optical window 101 in Ti-Sapphire material may have a quantum property that can be stimulated by the LED arrays 205. As the LED arrays 205 as a light source provide photons into the optical window 101, a population inversion may take place and energy states of the optical window 101 in Ti-Sapphire may change. As a result of the amplification, the photons pumped into the optical window 101 may be amplified in the process to stimulate an emission of new photons that are coherent to the pumped photons by the LED arrays 205. For example, when the optical window 101 may be pumped with wavelength bandgaps between 495 nm and 560 nm, the optical window 101 may luminesce an amplified amount of light in wavelength bandgaps of 600-750 nm. Such solid-state amplification without an additional device may stimulate gains that ultimately exceed losses, in terms of the light energy being pumped and the amount that is luminesced with a gain factor. As noted above, such effects may be achieved through a favorable temperature gradient, which may be readily achieved in most cases by a wearable device. In low power applications such as this, the temperature gradient in most environments is conducive to the amplification of the pumped LED light with an extremely high gain factor. This means that the lenses may provide higher optical power outputs than would be expected based on the electrical power actually supplied by the LEDs.

It may be contemplated, in some exemplary embodiments, that the photovoltaics provided in the present design may be translucent, and may be applied directly over the lenses, so that all of the light provided by the lenses may pass through the photovoltaics and some of the light may be harvested by the translucent photovoltaics. This may ensure that, when the system is operating with a given favorable temperature gradient, the light provided by the lenses may be harvested indefinitely, with the photovoltaics supplying any necessary electrical power to operate the LEDs endlessly so long as similar efficiency gains can be maintained. It must of course be noted that translucent photovoltaics have a very low absorption efficiency at the thickness and surface area provided in this exemplary embodiment, meaning that not all light provided by the glasses will be obstructed by the photovoltaics. It is also noted that the user will be making use of the glasses in what is likely to be a lit environment, and as such the photovoltaics may operate on light other than that supplied by the LEDs, such as sunlight or other ambient light, in order to maintain the power sources in the glasses.

Figure 3:
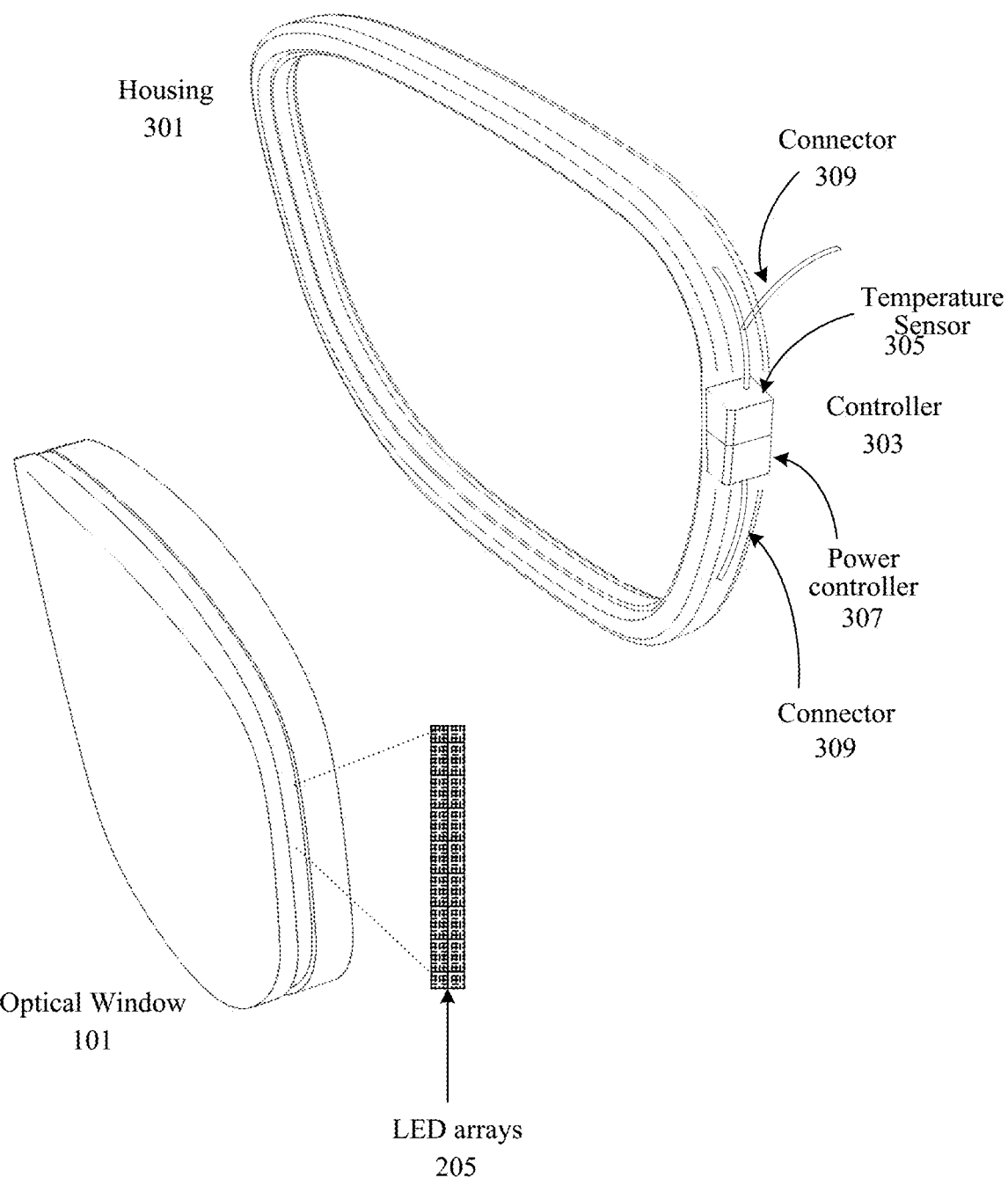
FIG. 3 is an exemplary schematic diagram showing a housing and at least one controller.

Turning now to exemplary FIG. 3, an exemplary schematic diagram showing a housing 301 and at least one controller 303 may be shown and described. According to an exemplary embodiment, an optical window 101 holding an interchangeable LED array 205 in the edges of the optical window 101 may be inserted into an optomechanical housing 301. For each LED array 205, the housing 301 may include the at least one controller 303 which is configured to have at least one temperature sensor 305 and at least one power controller 307. While the at least one temperature sensor 305 may monitor the temperatures of each LED arrays 205, the at least one power controller 307 may adjust input wattages via at least one connector 309 to individual LED arrays 205 based on temperatures monitored by the at least one temperature sensor 305. Such system provides the optical window 101 with the LED arrays 205 at optimal performance, by utilizing heat from the LED arrays 205 as a signal for the at least one power controller 307 to adjust input wattages. Since as the LED arrays 205 are heated, less wattage is required to maintain outputs from the LED arrays 205, such variable control may allow for the LED arrays 205 to maintain optimal thermal conditions. Therefore, the housing 301 may snap around the edges of the optical window 101 and maintain the power amplification ecosystem for solid-state amplification within the optical window 101 without an additional device for such amplification.

In still further exemplary embodiments, the system may be configured to have a high precision of the optomechanical housing 301 and integrated components in order to establish interchangeable components scheme in the system for either future upgrades to improve efficiencies of the current system or degradations to replace parts of the system. Particularly, the optomechanical housing 301 and related elements may be housed in a "bay system" so that the elements in the housing 301 may be slid in and out of individually. Furthermore, each of the at least one controller 303 of the housing 301 may contact via the at least one connector 309 which may directly plug into the at least one controller 303.

Figure 4:
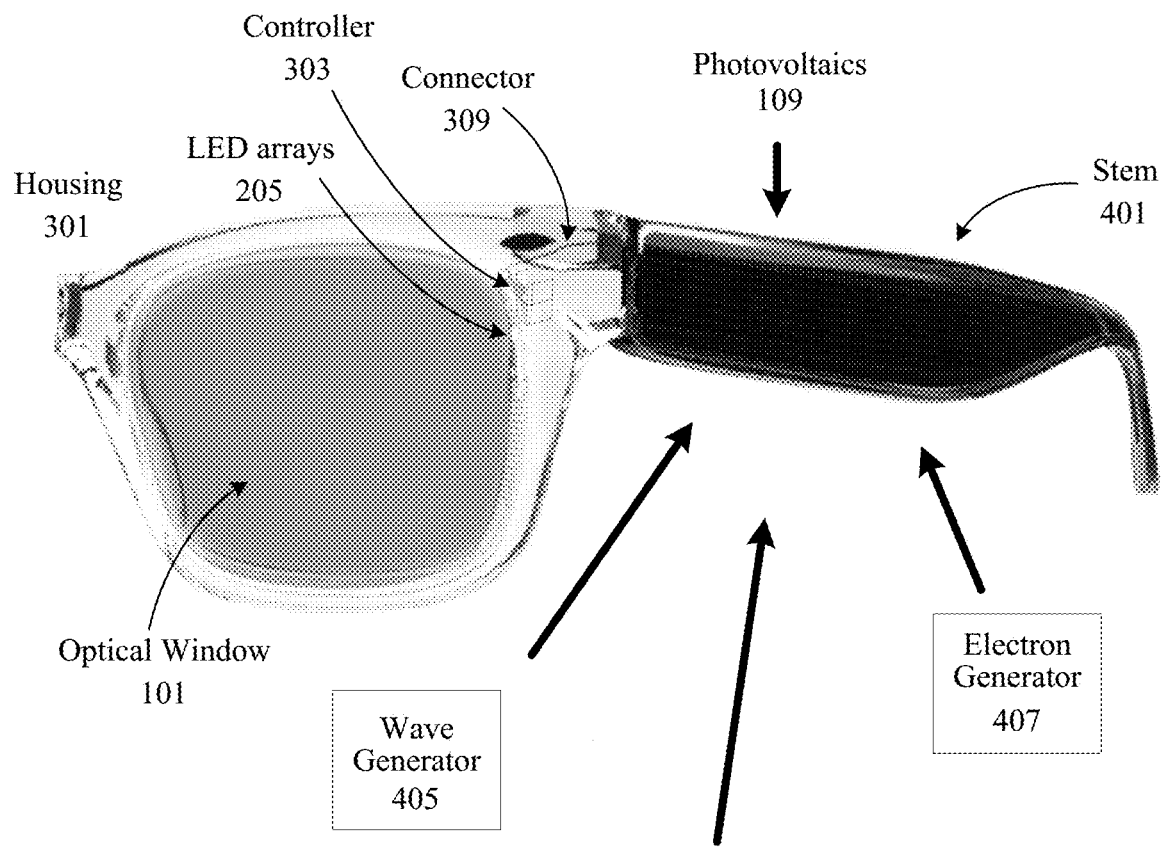
FIG. 4 is an exemplary schematic diagram showing a stem of a housing which includes a control panel, at least one photovoltaics, at least one wave generator, and at least one electron generator.
Figure 4:
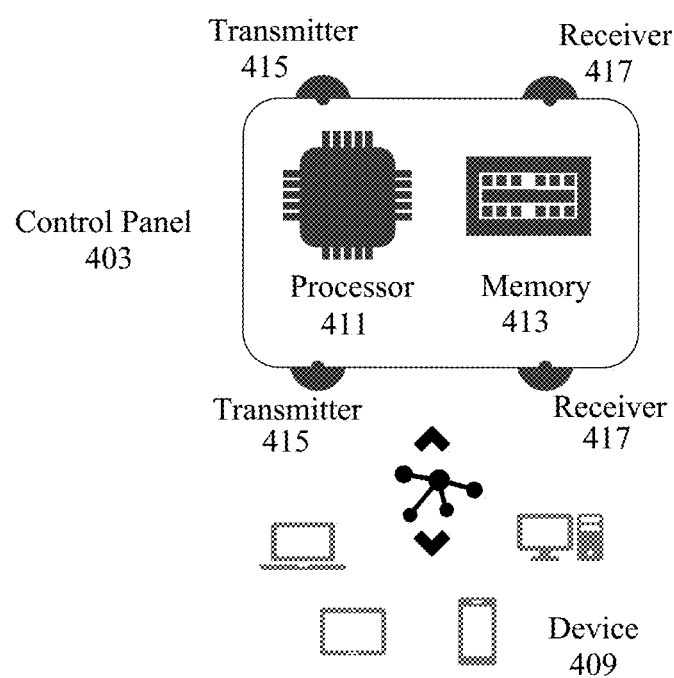

Turning to exemplary FIG. 4, an exemplary schematic diagram showing a temple, or stem 401, of a housing 301 which may include a control panel 403, at least one photovoltaic cell 109, at least one wave generator 405, and at least one electron generator 407 may be shown and described. According to an exemplary embodiment, the at least one photovoltaic cell 109, such as Gallium Arsenide (GaAs) photovoltaic cells, may be placed in the stem 401 of the housing 301 to absorb ambient light energy. The at least one photovoltaics 109 is interchangeable and hold layers within microns of each other layers for optimal absorption and functional efficiencies. Particularly, a width of the stem 401 including the at least one photovoltaic cell 109 may be adjusted to receive maximum amount of ambient light energy from the environment whilst maintaining reasonable aesthetics. Moreover, available electricity generated by the at least one photovoltaics 109 may be regulated by a solid-state transistor in a way that the contacts from the at least one photovoltaics 109 to the at least one wave generator 405 or the at least one electron generator 407 may function as an inline capacitor in order to maintain slow charge-up and discharge to the contacts at a rate dependent upon the available ambient power. Furthermore, the electricity converted by the at least one photovoltaics 109 in an optical window 101 and the stem 401 may be transferred via connectors 309 to be consumed by any components of the system.

In still further exemplary embodiments, a stem 401 may contain at least one electron generator 407 for electro-acupuncture that algorithmically pulse current to acupuncture points near to the stem 401 is placed. The at least one electron generator 407 may provide a simple low-profile electrode in order to fasten on the acupuncture target area and then to the contact. As noted, it is noted that other systems for electrostimulation may be contemplated other than an acupuncture needle, such as any and all MENS devices (or even, in some circumstances, devices capable of supplying more than a microcurrent, if desired). For example, in an exemplary embodiment, an alligator-type clip may be used. In other cases, electro-acupuncture that involved full piercing may be used; in such cases, it may be contemplated for a terminal to be placed through the ear into the appropriate acupoint in order to provide a piercing. It may, for example, be contemplated to have this feature have a small electrode attached to it, with the opposite end having a magnetic contact that automatically snaps into the electro terminal on the back fin of the glasses, the rearmost part of the temple. This may ensure that the glasses are seamlessly integrated with the ear, when both putting glasses on and taking them off.

In additional exemplary embodiments, the stem 401 may contain the at least one wave generator 405 which has a coil to emit low decibel binaural stimulation to the ear cavity from where the at least one wave generator 405 is positioned on an end side of the stem 401. As noted above, binaural stimulation may be used to alter brain waves in a manner similar to meditation. For example, it may be employed for anxiety and mood control, focus or other various purposes, but also for the use in combatting auditory hallucinations in those that have schizo-effective disorder. Certain frequencies may be found to stimulate parts of the auditory system within the brain, overcoming these symptoms.

In still further exemplary embodiments, the control panel 403 of the system may function as a control center to enable load distribution and yield optimization of electricity usage in the system and amount of the photons pumped into the optical window 101 in order to ensure self-sustainability of the system in terms of power and independency from the grid. For such purpose, the control panel 403 may collect via the connectors 309 various data including all the relevant functional variables, such as, but not limited to, supplied wattage, demand wattage, and a degree of amplification. More particularly, individualized LED temperatures and input wattages from the at least one controller 303, a wave status from the at least one wave generator 405 and an electron status from the at least one electron generator 407 may be communicated with the control panel 403 via the connectors 309. The various data sent to the control panel 403 may be received by a receiver 417 and sent to a processor 411 in a control panel 403 to be analyzed by a corresponding set of computer instructions stored in memory 413. Subsequently, multiple tasks may be sent out by a transmitter 415 via connector 309 to take necessary actions required according to the analysis. Furthermore, in other exemplary embodiments, the control panel 403 may be associated with software and/or a software application (or "app") of device 409, which can be viewed on a mobile phone, tablet, computer, or the like. Further, data communication and transmission between the control panel 403 and any associated software and/or software application (or "app") of device 409 may be made in a wired or wireless fashion.

Still additional exemplary embodiments, components and wiring with a minimum number of layers and contacts may be casted into the housing 301 of the system's translucent polymer, which may employ a standard amorphous chip housing which may function as a surface mount chip. Additionally, materials may either be fused as one seamless component or placed into the housing 301 to hold components in place. Moreover, lithography etchings may also be utilized to leave all circuitry seamlessly integrated into the optical window 101. Furthermore, the system may be used in conjunction with sight prescriptions because as the optical window 101 fabricated, photovoltaics may be fused directly to faces of the optical window 101 for absorption of ambient light energy, and LED arrays 205 may be fused into grooves of the edge of the optical window 101 with nanoelectrodes attached for electrical connections to the controllers 303 inserted in the housing 301.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system for providing a turnkey neurological solution, comprising:
    at least one optical window provided on a front of a housing;
    at least one light source; and
    the housing having:
        at least one controller;
        at least one stem comprising a retaining structure configured to retain the system on an ear of the user;
        at least one connector disposed between the at least one stem and the at least one optical window;
        at least one photovoltaic element;
        at least one wave generator configured to emit binaural stimulation, said wave generator disposed on an inner surface of the housing configured to face the user, said at least one wave generator disposed at an end side of the stem; and
        one or more electrodes configured to supply the user with electro-acupuncture, said one or more electrodes disposed adjacent to the retaining structure and configured to contact the ear of the user;
    wherein the at least one optical window passes lights generated by the at least one light source,
    wherein the at least one optical window is mounted on the housing,
    wherein the at least one stem is extended from the housing, and
    wherein the at least one photovoltaic element is provided on the front of the housing.

2. The system of claim 1, wherein the at least one optical window is configured to amplify the lights received from the at least one light source, wherein the optical window is configured to luminesce amplified light in a different bandgap than the lights received from the at least one light source.

3. The system of claim 1, wherein the at least one optical window is angularly oriented and configured to direct the lights in a predetermined direction and is coated on one face of the at least one optical window with a reflective coating configured to reflect the lights in the predetermined direction.

4. The system of claim 1, wherein the at least one photovoltaic element comprises a plurality of photovoltaic cells provided in the at least one optical window and further comprising a gain medium, said photovoltaic cells configured to generate electricity and send the electricity via the at least one connector.

5. The system of claim 1, wherein the at least one optical window includes at least one groove around one or more outer edges of the at least one optical window, the at least one groove configured to hold the at least one light source in a predetermined angle of the at least one light source.

6. The system of claim 1, wherein the at least one light source is a plurality of interchangeable LED arrays connectable to the at least one controller.

7. The system of claim 1, wherein the at least one controller comprises:
    a temperature sensor; and
    a power controller,
    wherein the temperature sensor is configured to detect a temperature of the at least one light source, and
    wherein the power controller receives electricity via the at least one connector and manages a load distribution of the electricity according to the temperature detected by the temperature sensor.

8. The system of claim 1, wherein the at least one stem includes the at least one photovoltaic element, wherein the at least one photovoltaic element is configured to generate electricity and send the electricity via the at least one connector.

9. The system of claim 1, wherein the at least one stem includes at least one stimulator, said at least one stimulator including at least one of: the wave generator configured to provide binaural stimulation, and an electron generator having an exposed electrode configured to provide a microcurrent, said exposed electrode included in the one or more electrodes, wherein the at least one stimulator is electrically powered via the at least one connector.

10. The system of claim 1, further comprising a control panel, wherein the control panel includes:
    at least one processor;
    at least one memory operably connected to the at least one processor;
    at least one transmitter; and
    at least one receiver,
    wherein the control panel is connected to the at least one controller and configured to provide a communication to the at least one controller.

11. A method for providing a turnkey neurological solution, comprising:
- absorbing, with at least one photovoltaic element, ambient light, and generating lights by at least one light source via power supplied by the at least one photovoltaic element;
- passing, by at least one optical window that is configured to direct the generated lights in a predetermined direction based on a combination of an angular orientation of the at least one optical window configured to direct the generated lights in a predetermined direction and a coating provided on one face of the at least one optical window configured to direct the generated lights in the predetermined direction, said predetermined direction comprising a user-determined incident angle configured to direct light from the at least one light source into an eye of the user;
- detecting, with one or more sensors comprising at least a temperature sensor, at least one operating state value of the at least one light source; and
- controlling, by at least one controller, a wattage of the at least one light source from a first non-zero value to a second non-zero value based on the operating state value of the at least one light source,
- wherein the at least one optical window is mounted on a housing,
- wherein the housing includes the at least one controller, at least one connector and at least one stem,
- wherein the at least one stem is extended from the housing; and
- wherein the at least one photovoltaic element and the at least one optical window are each provided on a front of the housing.

12. The method of claim 11, wherein the at least one optical window amplifies the lights received from the at least one light source, wherein the optical window is configured to luminesce amplified light in a different bandgap than the lights received from the at least one light source.

13. The method of claim 11, wherein the at least one photovoltaic element comprises a plurality of photovoltaic cells provided in the at least one optical window and further comprising a gain medium, said photovoltaic cells to generate electricity and send the electricity via the at least one connector.

14. The method of claim 11, wherein the at least one optical window includes at least one groove around outer edges of the at least one optical window to hold the at least one light source in a predetermined angle of the at least one light source.

15. The method of claim 11, wherein the at least one light source is interchangeable LED arrays connectable to the at least one controller.

16. The method of claim 11, wherein the at least one controller includes a power controller, wherein the method comprises:
- detecting, with the at least one temperature sensor, a temperature of the at least one light source;
- receiving, with the power controller, electricity via the at least one connector; and
- managing a load distribution of the electricity according to the temperature detected by the at least one temperature sensor.

17. The method of claim 11, wherein the at least one stem includes the at least one photovoltaic element configured to generate electricity and send the electricity via the at least one connector.

18. The method of claim 11, wherein the at least one stem includes at least one stimulator having at least one of a wave generator configured to provide binaural stimulation and an electron generator having an exposed electrode configured to provide a microcurrent, wherein the at least one stimulator is electrically powered via the at least one connector.

19. The method of claim 11, wherein a control panel is connected to the at least one controller and configured to provide a communication to the at least one controller, wherein the control panel includes at least one processor, at least one memory operably connected to the at least one processor, at least one transmitter, and at least one receiver.

* * * * *